United States Patent
Kutikov et al.

(10) Patent No.: US 9,949,630 B2
(45) Date of Patent: Apr. 24, 2018

(54) MEDICAL INSTRUMENT SYSTEM AND METHOD FOR MANIPULATING TARGET TISSUE

(75) Inventors: Alexander Kutikov, Cherry Hill, NJ (US); Thomas Fitzsimons, Swarthmore, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 3 days.

(21) Appl. No.: 12/938,794

(22) Filed: Nov. 3, 2010

(65) Prior Publication Data

US 2011/0105841 A1    May 5, 2011

Related U.S. Application Data

(60) Provisional application No. 61/257,919, filed on Nov. 4, 2009.

(51) Int. Cl.
*A61B 10/00* (2006.01)
*A61B 1/307* (2006.01)
(Continued)

(52) U.S. Cl.
CPC ........... *A61B 1/307* (2013.01); *A61B 5/6839* (2013.01); *A61B 5/6882* (2013.01);
(Continued)

(58) Field of Classification Search
CPC . A61B 1/00126; A61B 1/018; A61B 1/00154; A61B 1/05; A61B 1/053;
(Continued)

(56) References Cited

U.S. PATENT DOCUMENTS 5,842,973 A * 12/1998 Bullard ................... 600/194
6,730,084 B2    5/2004 Held
(Continued)

FOREIGN PATENT DOCUMENTS

AU    2003250220        5/2004
AU    2003276031 A1    5/2004
(Continued)

OTHER PUBLICATIONS

Bianco Jr., Fernando J.; Justa, Daniel; Grignon, David J.; Sakr, Wael A.; Pontes, J. Edson; Wood, Jr., David P.; "Management of Clinical T1 Bladder Transitional Cell Carcinoma by Radical Cystectomy;" Urologic Oncology: Seminars and Original Investigations 22; pp. 290-294; 2004.
(Continued)

*Primary Examiner* — Devin Henson
(74) *Attorney, Agent, or Firm* — RatnerPrestia

(57) ABSTRACT

A method is provided for manipulating target tissue of a patient during a medical procedure. The method includes introducing a medical instrument system to a general site of target tissue. At least one characteristic of the target tissue is identified using an imaging device located in a working channel of the medical instrument system. The imaging device is removed from the working channel of the medical instrument system, and a medical instrument is inserted through the working channel of the medical instrument system. The target tissue is then manipulated using the medical instrument. A medical instrument system is also provided for manipulating target tissue of a patient during a medical procedure.

6 Claims, 12 Drawing Sheets

(51) Int. Cl.
*A61B 5/00* (2006.01)
*A61B 10/02* (2006.01)
*A61B 90/00* (2016.01)
*A61B 18/00* (2006.01)
*A61B 17/34* (2006.01)
*A61B 17/00* (2006.01)
*A61B 10/04* (2006.01)

(52) U.S. Cl.
CPC ...... *A61B 10/0233* (2013.01); *A61B 10/0283* (2013.01); *A61B 10/04* (2013.01); *A61B 2017/0034* (2013.01); *A61B 2017/00349* (2013.01); *A61B 2017/3484* (2013.01); *A61B 2017/3488* (2013.01); *A61B 2018/00273* (2013.01); *A61B 2018/00279* (2013.01); *A61B 2090/3991* (2016.02)

(58) Field of Classification Search
CPC ....... A61B 1/012; A61B 1/0125; A61B 1/307; A61B 10/0233; A61B 10/0283; A61B 10/04; A61B 5/6839; A61B 5/6882; A61B 2017/3484; A61B 2017/3488; A61B 2017/00349; A61B 2018/00273; A61B 2018/00279; A61B 2090/3991; F16L 37/084
USPC .................................. 600/104, 562, 585
See application file for complete search history.

(56) References Cited

U.S. PATENT DOCUMENTS

| | | | |
|---|---|---|---|
| 6,860,848 B2 | 3/2005 | Wosnitza et al. | |
| 7,422,589 B2 | 9/2008 | Newton et al. | |
| 7,488,318 B2 | 2/2009 | Aue et al. | |
| 7,794,393 B2 | 9/2010 | Larsen | |
| 7,815,639 B2 | 10/2010 | Brommersma | |
| 2002/0045855 A1* | 4/2002 | Frassica | 604/109 |
| 2002/0077555 A1* | 6/2002 | Schwartz | 600/486 |
| 2002/0087169 A1* | 7/2002 | Brock et al. | 606/139 |
| 2003/0073908 A1 | 4/2003 | Desai | |
| 2004/0127893 A1* | 7/2004 | Hovda | 606/15 |
| 2004/0171916 A1* | 9/2004 | Brommersma | 600/162 |
| 2005/0010080 A1 | 1/2005 | Dickopp | |
| 2006/0015007 A1 | 1/2006 | Aue et al. | |
| 2006/0058580 A1 | 3/2006 | Reichenbach et al. | |
| 2006/0094930 A1* | 5/2006 | Sparks et al. | 600/104 |
| 2006/0122459 A1 | 6/2006 | Aue | |
| 2006/0149129 A1* | 7/2006 | Watts | A61B 1/00135 600/113 |
| 2007/0135792 A1* | 6/2007 | Pierpont et al. | 604/509 |
| 2007/0167828 A1* | 7/2007 | Saadat | 600/463 |
| 2007/0191676 A1 | 8/2007 | Brommersma | |
| 2007/0225554 A1* | 9/2007 | Maseda | A61B 1/018 600/104 |
| 2007/0244353 A1* | 10/2007 | Larsen | 600/105 |
| 2007/0270642 A1* | 11/2007 | Bayer | A61B 1/0005 600/109 |
| 2008/0077129 A1 | 3/2008 | Van Wyk et al. | |
| 2008/0183038 A1* | 7/2008 | Tilson et al. | 600/104 |
| 2008/0188868 A1* | 8/2008 | Weitzner et al. | 606/130 |
| 2008/0228193 A1* | 9/2008 | Matityahu | A61M 37/0069 606/99 |
| 2008/0312496 A1* | 12/2008 | Zwolinski | 600/104 |
| 2009/0171152 A1* | 7/2009 | Aoki et al. | 600/114 |
| 2009/0240143 A1* | 9/2009 | Osdoit et al. | 600/431 |
| 2009/0312645 A1* | 12/2009 | Weitzner et al. | 600/476 |
| 2009/0318798 A1* | 12/2009 | Singh et al. | 600/424 |

FOREIGN PATENT DOCUMENTS

| | | |
|---|---|---|
| AU | 2003277930 A | 5/2004 |
| DE | 10126541 A1 | 12/2002 |
| DE | 10126541 B4 | 12/2002 |
| DE | 10126542 A1 | 1/2003 |
| DE | 10126542 B4 | 1/2003 |
| DE | 10139444 A1 | 3/2003 |
| DE | 10139444 B4 | 3/2003 |
| DE | 10139449 C1 | 4/2003 |
| DE | 10242608 A1 | 4/2004 |
| DE | 10248836 A1 | 5/2004 |
| DE | 10248839 A1 | 5/2004 |
| DE | 102004045337 A1 | 4/2006 |
| DE | 102005032821 A1 | 1/2007 |
| DE | 102005057933 | 6/2007 |
| DE | 102006006950 A1 | 8/2007 |
| DE | 202006020071 U1 | 9/2007 |
| DE | 102007010442 A1 | 9/2008 |
| EP | 1392184 A1 | 3/2004 |
| EP | 1392184 B1 | 3/2004 |
| FR | 2825259 A1 | 12/2002 |
| GB | 2377643 A | 1/2003 |
| GB | 2394422 A | 4/2004 |
| GB | 2394422 B | 4/2004 |
| GB | 2408688 A | 6/2005 |
| GB | 2408688 B | 6/2005 |
| GB | 2408689 A | 6/2005 |
| GB | 2408689 B | 6/2005 |
| GB | 2408942 A | 6/2005 |
| GB | 2408942 B | 6/2005 |
| JP | 2005537901 T | 12/2005 |
| JP | 2007152091 A | 6/2007 |
| JP | 2007216006 | 8/2007 |
| WO | WO 02096305 A | 12/2002 |
| WO | WO 02096305 A1 | 12/2002 |
| WO | WO 2003013347 A | 2/2003 |
| WO | WO 2003013347 A1 | 2/2003 |
| WO | WO 2003013378 A | 2/2003 |
| WO | WO 2003013378 A1 | 2/2003 |
| WO | WO 2004032732 A1 | 4/2004 |
| WO | WO 2004037100 A1 | 5/2004 |
| WO | WO 2006023456 A2 | 3/2006 |
| WO | WO 2007121109 A2 | 10/2007 |
| WO | WO 2007121109 A3 | 10/2007 |
| WO | WO 2008039746 A2 | 4/2008 |
| WO | WO 2008039746 A3 | 4/2008 |
| WO | WO 2008104275 A1 | 9/2008 |
| WO | WO 2004037101 A1 | 5/2009 |

OTHER PUBLICATIONS

Hall, M. Craig; Chang, Sam S.; Dalbagni, Guido; Pruthi, Raj Som; Seigne, John Derek; Skinner, Eila Curlee; Wolf, Jr., J. Stuart and Schellhammer, Paul F., "Guideline for the Management of Nonmuscle Invasive Bladder Cancer (Stages Ta, T1, and Tis): 2007 Update;" The Journal of Urology, VO1. 178; pp. 2314-2330; Dec. 2007.

Clarke, H.C., "Laparoscopy: New Instruments for Suturing and Ligation," Fertility and Sterility; vol. 23, No. 4; pp. 274-277; Apr. 1972.

Hoshi, S.; Ono, K.; Suzuki K.; Ohyama, C.; Namima, T.; Orikasa, S.; "Trans-Urethral Whole Layer Core Biopsy for Detection of Residual Tumor After Neoadjuvant Therapy in Invasive Bladder Cancer;" Urologic Oncology 6; pp. 85-89; May 2001.

Nieder, A.M.; Manoharan, M.; "The Role of the Surgeon and Transurethral Resection in the Treatment of Superficial Bladder Cancer;" Scientific World Journal 6; pp. 2626-2631; 2006.

* cited by examiner

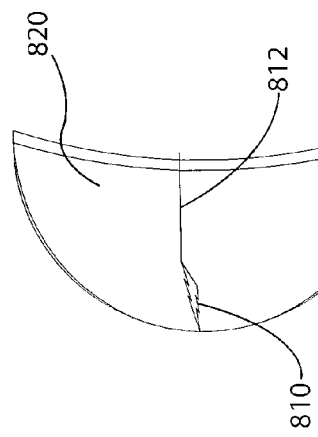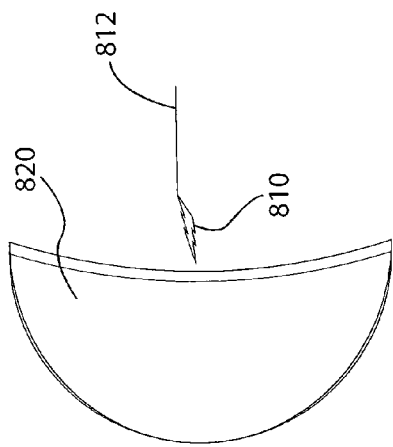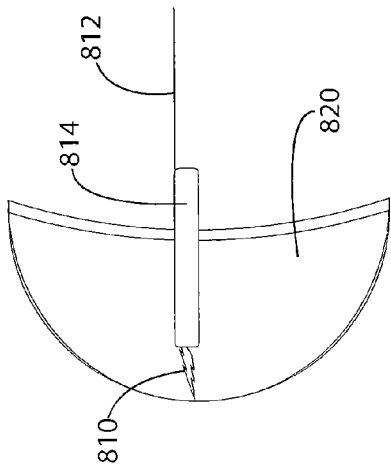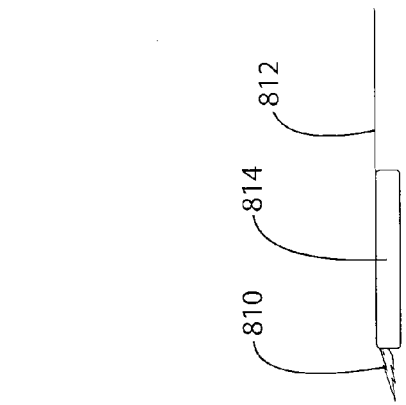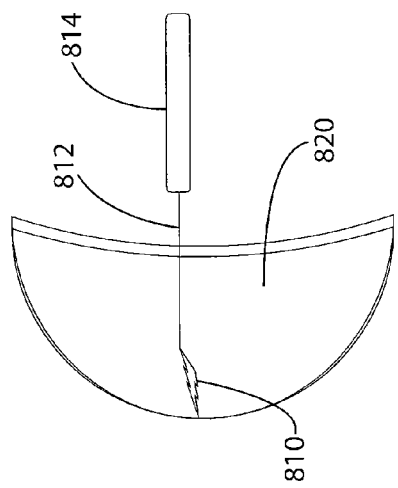

MEDICAL INSTRUMENT SYSTEM AND METHOD FOR MANIPULATING TARGET TISSUE

CROSS REFERENCE TO RELATED APPLICATIONS

This application claims priority to U.S. Provisional Application Ser. No. 61/257,919, filed Nov. 4, 2009, which is incorporated herein, in its entirety, by reference.

FIELD OF INVENTION

The present invention relates to a medical instrument system and method for manipulating target tissue of a patient during a medical procedure, in particular, manipulating target tissue in a patient during a bladder biopsy.

BACKGROUND OF THE INVENTION

Tissue manipulation is often required for the completion of certain medical procedures. It may be advantageous or necessary for example to remove a sample of tissue from a patient if it is determined to be diseased or suspected of being diseased. Such tissue manipulation may be a component of biopsy procedures like those used to determine whether tissue is cancerous.

Bladder cancer, for example, affects a great number of individuals throughout the world. Intravesical imaging and localized or site specific treatments are a standard of care for patients whose disease is in the early stages. Many lesions are difficult to reliably access and appropriately sample using current techniques. This is especially true of lesions located on the bladder dome, anterior bladder wall, or immediately adjacent to the bladder outlet. These clinical realities lead to less effective diagnosis and treatment for some lesions. Virtually all of these procedures, as well as similar procedures done on other organs such as the esophagus, are typically image guided by use of an endoscope.

Endoscopes have origins that date back to the early 1800s. Human medical use began to be a routine function of the endoscope beginning in the early 1900s with the introduction of laparoscopy. Virtually all improvements and modifications of endoscopes have been based on the desire for better and larger images from smaller and smaller devices.

Endoscopic surgery also dates to the early 1900s. It was drastically improved in 1970s when computer chip cameras were incorporated into endoscopes and its utility greatly expanded. See, for example, Clarke, H. C., Laparoscopy: New Instruments for Suturing and Ligation: Fertil. Steril. 23, 274 (1972). The endoscope has remained primarily an optical imaging system for the visual guidance of additional tools.

Current management of localized bladder cancer utilizes transurethral resection of balder tumor (TURBT) procedure in order to both treat and stage this malignancy. This procedure is typically performed using rigid (non-flexible) instrumentation and employs electrocautery for tissue procurement. Patients whose tumors do not invade the detrussor muscle of the bladder (such as Ta or T1 tumors), generally undergo intravesical chemotherapy and/or immunotherapy and close cystoscopic surveillance. Patients with early stage cancers are scoped approximately every 3 to 6 months. Recurrences are common.

Staging of bladder cancer with transurethral resection is currently the standard of care; however, staging inaccuracies are well-documented and present great clinical concern. In some studies, greater than 25% of patients with recurrent T1 disease (invasion into the bladder lamina propria but not into muscle) who undergo cystectomy are found to have been understaged with TURBT. Suboptimal sampling of the detrussor muscle and cautery artifact inherent to the procedure often results in missed diagnoses of T2 disease. These in turn stem from inherent limitations of modern transurethral instrumentation and from routine use of electrocautery to procure pathological tissue specimens. Understaging of T1 bladder urothelial carcinoma is underscored by a very troubling cancer-specific mortality rate of as high as 30%.

While various tissue manipulation systems and methods have been proposed, there remains a need for improved systems and methods for manipulating target tissue of a patient during a medical procedure such as a bladder biopsy. Improved safe and accurate staging of bladder cancer represents a goal with enormous clinical and scientific merit.

SUMMARY OF THE INVENTION

According to one aspect of the invention, a method is provided for manipulating target tissue of a patient during a medical procedure. The method includes introducing a medical instrument system to a general site of target tissue. At least one characteristic of the target tissue is identified using an imaging device located in a working channel of the medical instrument system. The imaging device is removed from the working channel of the medical instrument system, and a medical instrument is inserted through the working channel of the medical instrument system. The target tissue is then manipulated using the medical instrument.

According to another aspect of the invention, a medical instrument system is provided for manipulating target tissue of a patient during a medical procedure. The system includes an instrument system body; a working channel defined in the instrument system body; an imaging device having a cross-sectional shape sized to fit within the working channel defined by the instrument system body; a medical instrument having a cross-sectional shape sized to fit within the working channel defined by the instrument system body; and a fixation element positioned to fix at least one of the imaging device and medical instrument and configured to resist axial movement of the imaging device or the medical instrument in the working channel with respect to the instrument system body.

According to yet another aspect of the invention, a method for manipulating target tissue includes introducing a medical instrument system to a general site of target tissue, identifying at least one characteristic of the target tissue, and securing a distal end of the medical instrument system to resist movement with respect to the target tissue such that the distal end of the medical instrument system remains at a fixed position near the target tissue. The target tissue is then manipulated using a medical instrument introduced through a working channel defined by the medical instrument system. The distal end of the medical instrument system is then released to facilitate movement of the medical instrument system from the fixed position.

According to still another aspect of the invention, a medical instrument system includes an instrument system body, a fixation channel defined by the instrument system body, and means for releasably securing a distal end of the instrument system body to resist movement with respect to the target tissue such that the distal end of the instrument system body remains at a fixed position near the target tissue.

BRIEF DESCRIPTION OF THE DRAWINGS

The foregoing summary, as well as the following detailed description of exemplary embodiments of the invention, will be better understood when read in conjunction with the appended drawings, which are incorporated herein and constitute part of the specification. For the purposes of illustrating the invention, there are shown in the drawing, exemplary embodiments of the present invention. It will be understood, however, that the invention is not limited to the precise arrangements and instrumentalities shown. In the drawings, the same reference numerals are employed designating the same elements throughout the several figures. In the drawings:

FIGS. 8A through 8E illustrate a five-step embodiment of a method for manipulating the target tissue of a patient;

DETAILED DESCRIPTION OF THE INVENTION

Figure 1:
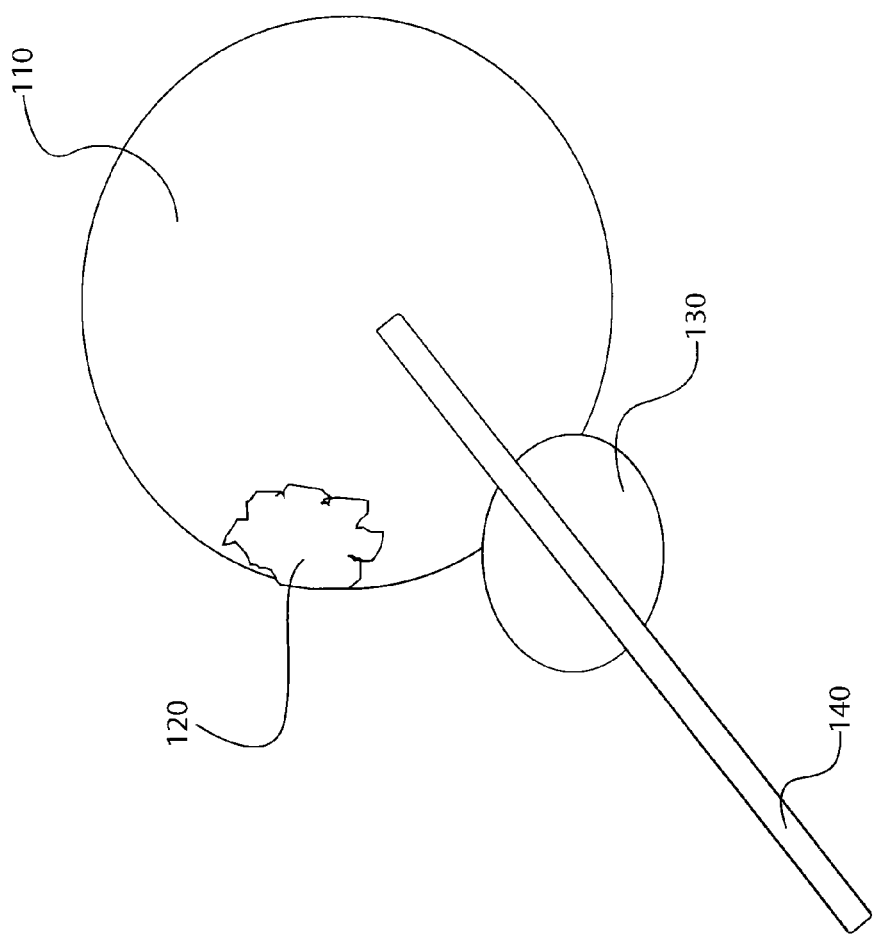
FIG. 1 is a diagram schematically depicting a patient's bladder with a tumor on the anterior bladder wall

Although the invention is illustrated and described herein with reference to specific embodiments, the invention is not intended to be limited to the details shown. Rather, various modifications may be made in the details within the scope and range of equivalents of the claims and without departing from the invention. The following description discloses primarily the use of the device for biopsy, but it will be understood to one skilled in the art that the invention relates to any endoscopic procedure that requires the use of an effecting tool other than the native imaging system within the endoscope. Embodiments of the invention illustrated and described herein increase the space available for effecting tools by allowing the removal of the high resolution optical imaging system, freeing up that space for other devices. Other devices that may utilize aspects of the invention may include a different imaging system with a smaller footprint, thereby giving more working space for effector tools with the same size through-the-skin entry hole.

The present invention relates to a device that can be used to effect target tissue, for example, to obtain a tissue sample, such as a through and through tissue sample of a bladder wall, in a precise, targeted and controlled fashion. Such a tissue sample may be obtained through Minimally Invasive Surgery (MIS) with an instrument such as an endoscope. An endoscope is an optical imaging device and typically consists of:

a rigid or flexible tube a light delivery system to illuminate the organ or object under inspection; the light source being normally outside the body and the light is typically directed via an optical fiber system a lens system transmitting the image to the viewer from the fiberscope an additional channel (working channel) to allow entry of medical instruments or manipulators While MIS has been widely adopted there are circumstances and organs where its utility could be improved by the development of novel instrumentation. In general, these are cases where adding additional access ports is impractical or impossible, or where the initial placement of the endoscope is time consuming, and where it is likely to be dislocated from its initial position by subsequent tool manipulation introduced either through the working channel or through an additional access port. This might be the case in organs where there is only one minimally traumatic access route to the target tissue as in the case in the bladder where the endoscope and subsequent tools are delivered through the urethra, and where placing additional ports percutaneously through the lower abdominal wall has unwanted side effects.

An additional improvement allows the operator of an endoscopic instrumentation to choose whatever tools are necessary for the procedural step to be performed at the time that that step is to be performed without the constraint of device intrinsic instrumentation that may not be needed at that point in the overall intervention. Since the goal of MIS is to minimize the surgical intervention, it is preferred to use access ports and working channels in devices, maximizing the utility and flexibility of those ports and working channels. A non-limiting example is endoscopy and endoscopic biopsy of the bladder.

Embodiments of the invention preferably provide one or more tissue anchors that is/are deployed into an area of concern on tissue such as the bladder wall under rigid or flexible cystoscopic guidance. Other examples may include the ablation or resection of target tissue. Tissue anchor placement may or may not use transvesical ultrasound guidance to further refine tissue targeting. The ultrasound probe and the anchor deployment device may or may not be an integrated device unit. Tissue anchor methodology proposed here obviates the need for electrocautery and thus eliminates the cautery artifact that so often limits modern transurethral tumor staging. Indeed, such delivery of core or cold-cut biopsy methodology into a hollow viscus through a flexible scope is novel.

Ultrasound, if used, may help define the depth of tissue penetration by the anchor according to exemplary embodiments of the invention. Tissue penetration by the anchor may use a screw and twist technology or another viable method to penetrate tissue in a controlled fashion. This tissue anchor will be attached to a guide-wire. An effector device such as a biopsy device then will be deployed onto the bladder wall over this guide-wire.

This medical instrument system may have imaging capabilities such as optical imaging or ultrasonographic imaging. The medical instrument system may convert a flexible delivery probe into a rigid instrument. Target tissue is obtained employing known coring techniques, spring-loaded core biopsy technology, or any other similar methods that employ core-biopsy-type methods. Such tissue sampling provides targeted tissue free of cautery artifact.

FIG. 1 shows a drawing of a male bladder 110 containing a tumor 120 and indicating the location of the prostate 130. Traditionally, to access a tumor located in bladder 110, a rigid transurethral resectoscope 140 is inserted in the urethra, which passes through the prostate 120 and into the bladder 110. Tumors that are located on the floor (the trigone) and lateral or posterior walls of the bladder subject themselves to relatively straightforward manipulation. Tumors that are located on the anterior bladder wall, bladder dome, or are immediately adjacent to the bladder outlet are difficult to visualize and sample using rigid instruments. Although modern flexible cystoscopes afford excellent visualization of such lesions, tissue manipulation and sampling through such scopes is currently limited and suboptimal for accurate staging of bladder cancer.

For example, to access the tumor 120 shown in FIG. 1, the distal end of transurethral resectoscope 140 must be bent at an angle greater than 90 degrees and possibly close to an angle of 180 degrees. Because of these difficulties in accessing tumors at challenging locations, it is difficult for surgeons to maintain multiple imaging devices, medical instruments, or biopsy components in the same target tissue area on which the tumor 120 is located.

In order to provide an improved method and system for manipulating target tissue of a patient such as the tissue within the bladder, disclosed herein is a medical instrument system that allows the user to not only guide the instrument body to the target tissue area, but then to also secure the instrument body to the target tissue and allow for the interchange of various components such as medical instruments, imaging devices and biopsy instruments.

Figure 2:
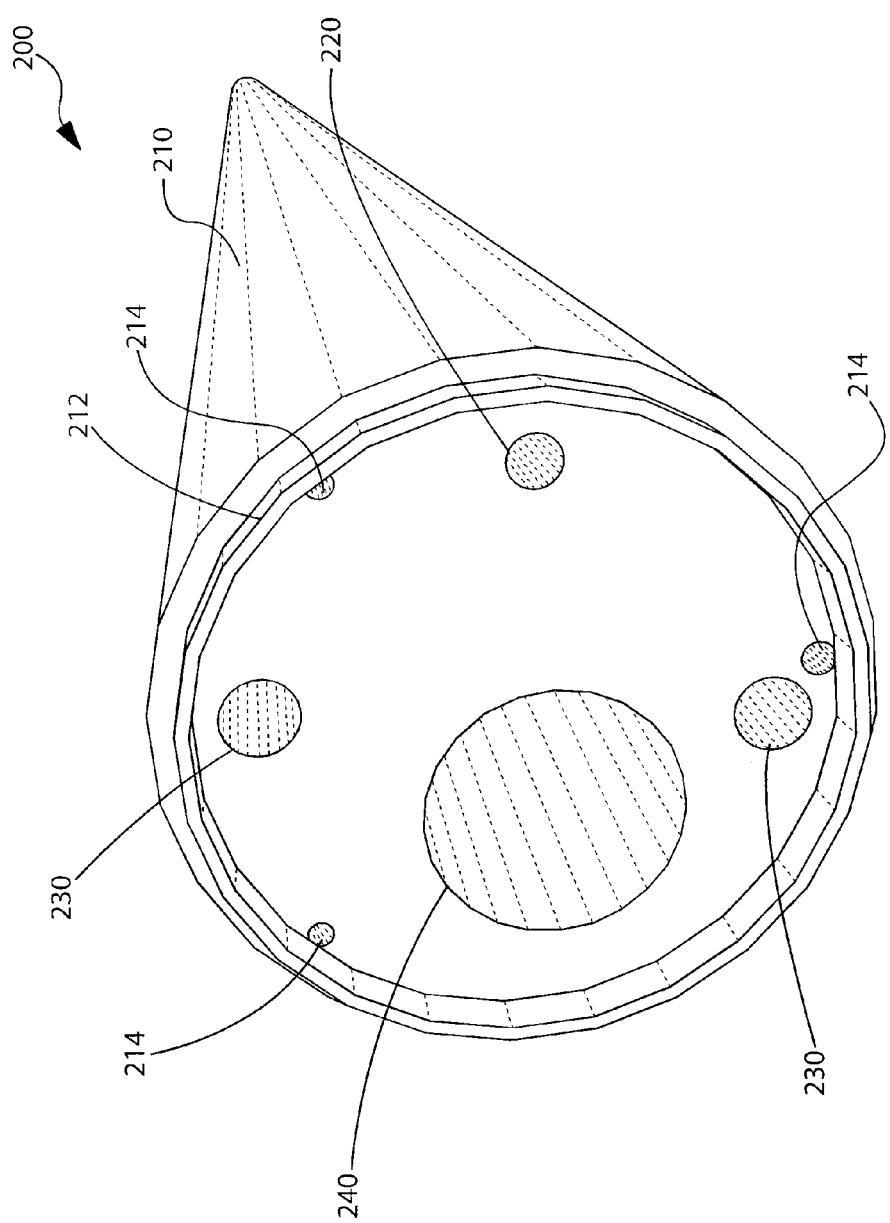
FIG. 2 is a perspective end view of the distal end of an embodiment of a system for manipulating target tissue of a patient during a medical procedure according to an aspect of the present invention.

FIG. 2 shows one such exemplary embodiment of this medical instrument system. In FIG. 2, the medical instrument system 200 consists of an elongated, flexible scope body 210. Flexible scope body 210 may be made of polyether block amide (PeBax) tubing or other similar material. A deflection ring 212 is located at the distal end of the scope body. Deflection ring 212 may act as a girdle or barrier to further extend the distal end of scope body 210. Additionally, deflection ring 210 may help to form a tight seal when the distal end of scope body 210 comes in contact with the target tissue area.

Scope body 210 also contains deflection wires 214 located evenly along the circumference or perimeter region of the scope body 210. Deflection wires 214 allow the flexible scope body 210 to be bent as needed to travel through the incision or to locate the target tissue. Once the scope is bent as needed, the deflection wires 214 may be secured to make the scope body 210 become rigid and thereby maintain the angle of the scope body 210.

In this embodiment of the medical instrument system 200, the scope body 210 defines three different types of channels. Scope body 210 defines a guide-wire channel 220 which allows for the insertion of a guide-wire. This guide-wire may be used to guide the scope to the proper location of the target tissue, to help secure the scope body 210 to the target tissue, or to deploy a biopsy sheath device for a core biopsy. Although only one guide-wire channel is shown in FIG. 2, it should be understood that scope body 210 may define any number of guide-wire channels 220 or conversely in some embodiments scope body 210 may not define any guide-wire channels 220 at all. Furthermore, the guide-wire channel 220 may be of any relevant size and is not limited to the size or shape illustrated in FIG. 2.

Scope body 210 also defines two fixation channels 230 through which suction may be applied. In one embodiment of this invention, when the distal end of the scope body 210 has come into contact with the target tissue, vacuum is applied to the proximal ends of the fixation channels 230 so that the distal end of scope body 210 is secured to the target tissue. In another embodiment of this invention, a fastening device such as a screw-type fastener may be introduced through one or more of the fixation chambers 230 to secure the distal end of the scope body 210 to the target tissue. As with the guide-wire channels, the scope body 210 is in no way limited in the number of fixation chambers 230 it defines. In some embodiments of this invention, there may be multiple fixation chambers 230. In other embodiments, there may be no fixation chambers 230 defined at all. Furthermore, fixation channel 220 may be of any relevant size and is not limited to the size disclosed in FIG. 2.

In the embodiment illustrated in FIG. 2, scope body 210 also defines a working channel 240. Working channel 240 is sized to fit components that may be inserted inside the channel. These components may include, but are not limited to, imaging instruments such as optical devices, ultrasound devises, optical coherence tomography devices, ramen scattering devices, confocal microscopy and other forms of imaging instruments known in the art. Additionally, these components may include medical instruments such as forceps, biopsy packages, and other forms of medical instruments known in the art.

As with the other channels discussed in this embodiment, working channel 240 may be of any relevant size and may appear in any relevant quantity and is not limited to the size depicted in FIG. 2 or to only one working channel as shown in FIG. 2. Also, the working channel 240 may have a variety of cross-sectional shapes and configurations and is not limited to the substantially circular cross-sectional shape shown for illustration purposes.

As shown in FIG. 2, working channel 240 may be used to shuttle both optical and ultrasound imaging instruments, as well as tools for biopsies, or ablation. There is sufficient room for another working channel in the embodiment illustrated in FIG. 2. Since the guide-wire will anchor the scope body 210 in place, continual optical monitoring may not be needed and space may thereby be freed up for tool use.

Figure 3:
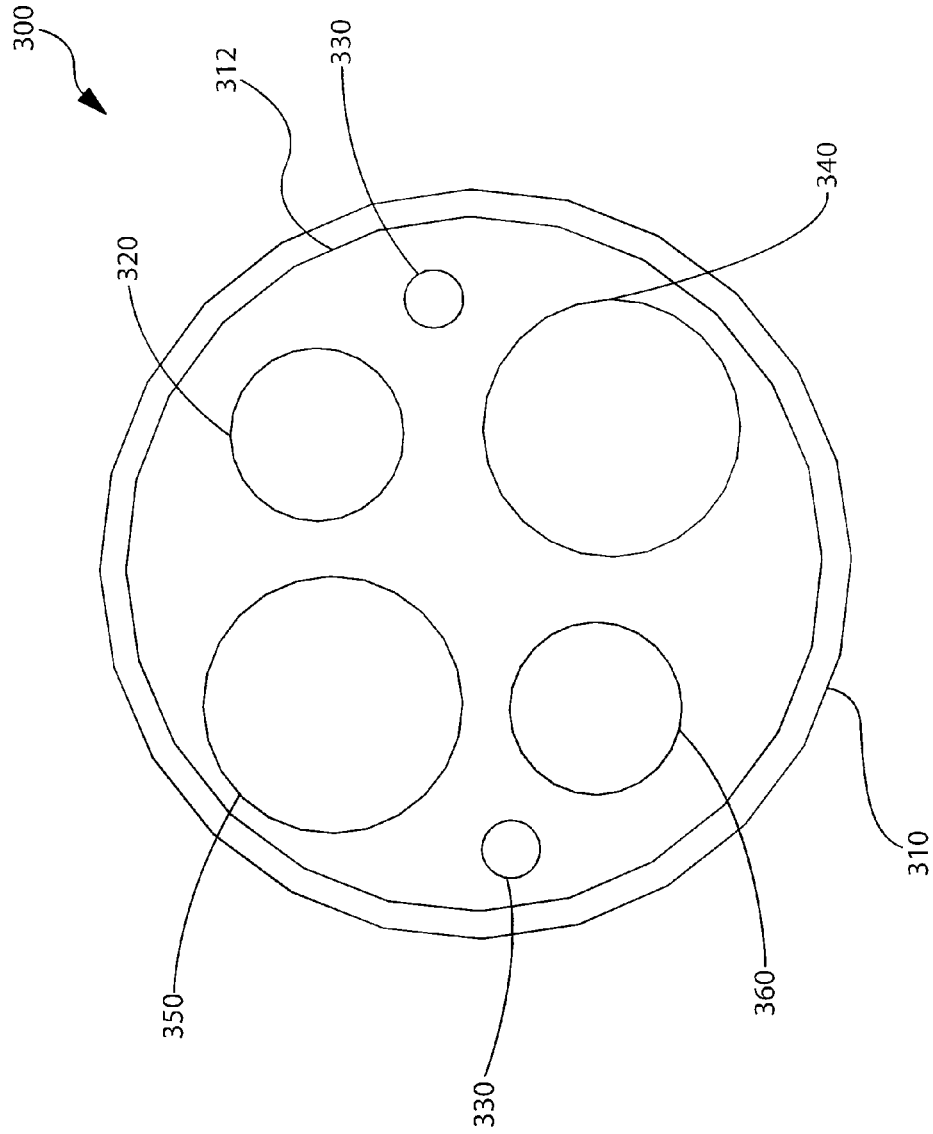
FIG. 3 is an end view of the distal end of another embodiment of a system for manipulating target tissue of a patient according to an aspect of the present invention.

FIG. 3 shows an end view of another embodiment of the medical instrument system 300, which is similar in some aspects to the system shown in FIG. 2. In this embodiment, scope body 310 contains a deflection ring 312 around the circumference of the ring. Scope body 310 defines a guide-wire channel 320 and two fixation channels 330. The guide-wire channel 320 and fixation channels 330 are not limited in quantity or size. In this embodiment of the medical instrument system, the scope body 310 also defines a working channel 340 as well as an optics channel 350 and an ultrasound channel 360.

In an alternative embodiment, an imaging device (not pictured) such as an optical imaging device may be permanently fixed in place or may be inserted through either a dedicated optics channel (such as optics channel 350) or in a working channel (such as working channel 340). Furthermore, dedicated imaging equipment such as ultrasound imaging equipment may be permanently fixed in place or may be inserted through either an optics channel (such as optics channel 350), a dedicated channel (such as ultrasound channel 306) or in a working channel (such as working channel 340).

The working channel defined by the body of the scope may have various different features that allow it to house interchangeable components. In one embodiment, the working channel will be defined by the scope body and the accompanying interchangeable components will be sized to fit snugly within the working channel or to be fixed within the working channel. In an alternative embodiment, the working channel is configured to guide or receive multiple interchangeable components.

Figure 4C:
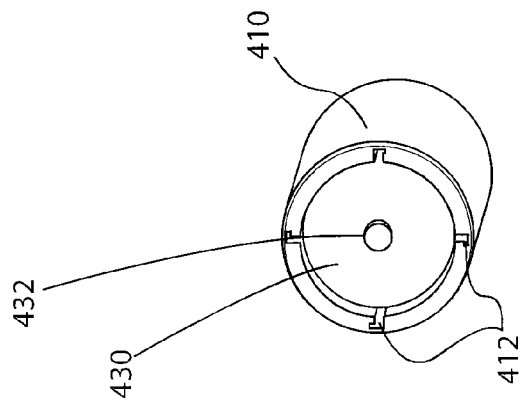
FIG. 4C is an enlarged perspective view of the system shown in FIG. 4A together with an anchoring balloon.
Figure 4B:
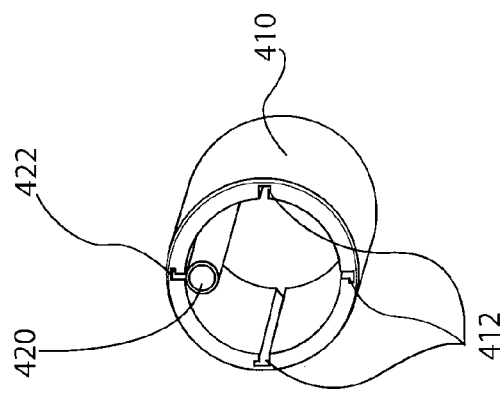
FIG. 4B is an enlarged perspective view of the system shown in FIG. 4A.
Figure 4A:
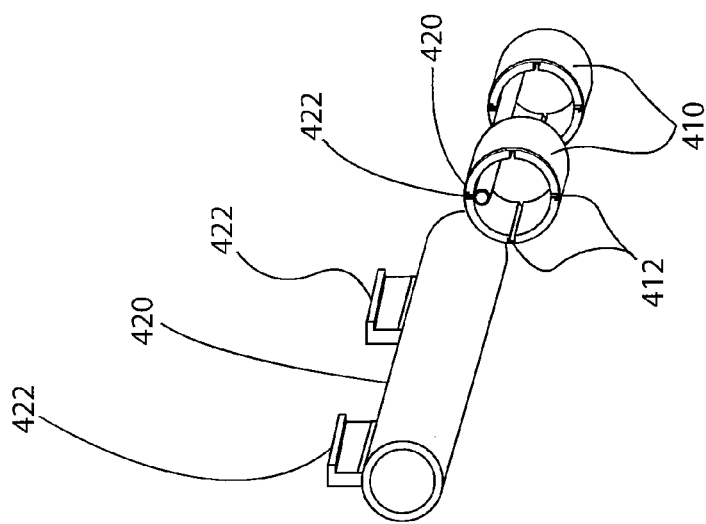
FIG. 4A is an exploded perspective view of yet another embodiment of a system for manipulating target tissue of a patient according to an aspect of the present invention, showing a segment of the system and an enlarged view of an imaging device component of the system.

In the embodiment depicted in FIGS. 4A through 4C, the working channel 410 is etched or otherwise provided with one or more key tracks 412 that are shaped to have a corresponding key 422 attached to an interchangeable component 420. Working channel 410 may be contain multiple key tracks 422 as shown in FIGS. 4A through 4C, or working channel 410 may be fit with only one key track. This allows more than one device to pass down the lumen without those devices interfering with each other within the lumen.

Once the interchangeable component 420 has been inserted into the working channel 410, the interchangeable component 420 may be secured at the proximal or distal end of the working channel through various means. As depicted in FIG. 4C, interchangeable component 410 is secured in place by means of an anchoring balloon 430. In this exemplary embodiment, upon insertion of the interchangeable component 420, anchoring balloon 430 may be inflated through a hand pump or other inflation source by the user. When anchoring balloon 430 is fully inflated, interchangeable component 420 is secured in place and will be prevented from moving axially with respect to the working channel. Imaging core 432, allows the user to maintain visual contact with any interchangeable components 410 that may be placed in the working channel 110 and secured in place by the anchoring balloon 430.

Figure 5:
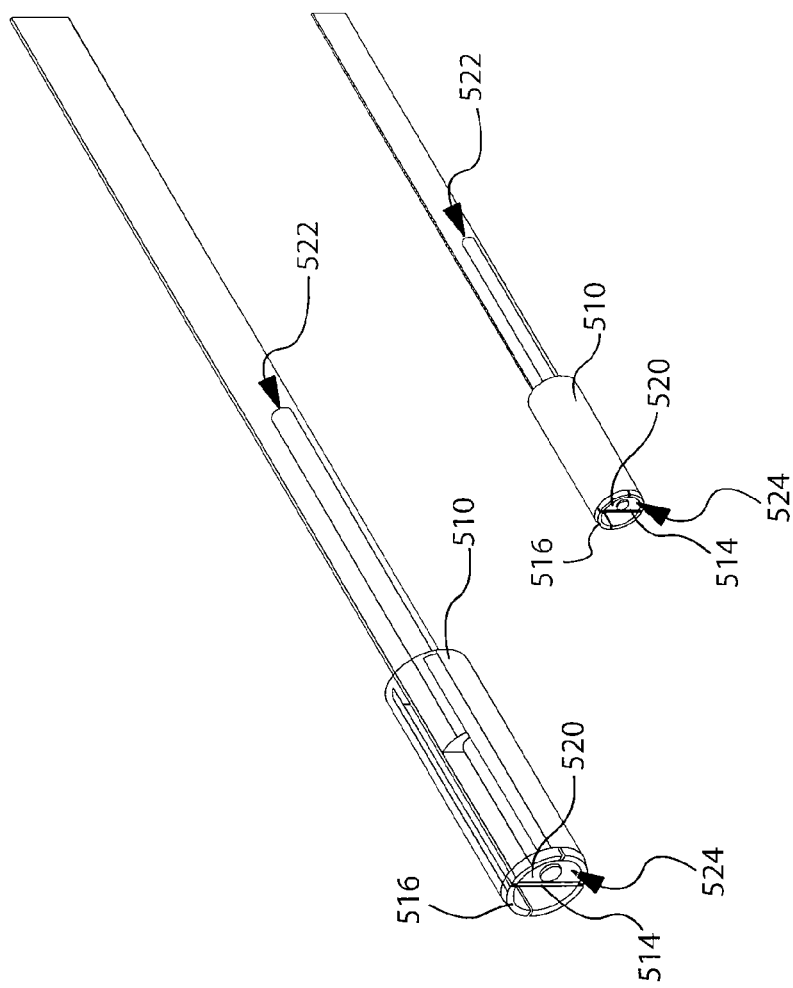
FIG. 5 is a perspective view of another embodiment of a system for manipulating target tissue of a patient according to an aspect of the present invention.

Another embodiment of a possible working channel is depicted in FIG. 5. In this embodiment of the working channel 510 contains a divider 514 which may be placed within the working channel to divide the overall space of the working channel into smaller channels. In this example, the divider bisects the working channel, cutting it in half. In this embodiment, interchangeable component 520 is sized to fit within just half of the working channel 510.

Proximal end 522 of interchangeable component 520 extends towards the proximal end of the working channel to allow the user access to the component. Distal end 524 of interchangeable component 520 may extend to the distal end 516 of the working channel to allow for proper use of the interchangeable component. By dividing working channel 510 into two parts, a second interchangeable component may be inserted in the unoccupied half of the working channel 510. As before, the interchangeable component 520 that has been fit in the working channel may be secured at a proximal end (not pictured) to prevent or resist axial movement of the interchangeable component 520 with respect to the working channel. Furthermore, it is understood that working channel 510 may be subdivided in any number of equal or unequal ways and shapes, not just by a divider 514 bisecting the working channel 510 as depicted in FIG. 5.

As discussed above, once an interchangeable component has been inserted into a working channel, the interchangeable component may be secured or otherwise held in place in the working channel through a various means such as screwing the interchangeable component into place, using a lock and lever system, or a suction balloon system.

Removing the optics equipment from a main channel, while a side channel still has optics capabilities that are of lower quality, allows the user to have a scout image that aids work during the tissue manipulation procedure. In many cases the purpose of medical imaging has been achieving better images faster. In endoscopy this has led to higher and higher resolution scopes, and thus better images. For diagnostic purposes, and for guidance to crucial target tissue this is important. Once the target tissue has been identified, located and reached by the proximal end of the medical instrument system, however, hi-resolution optics may not be as necessary, especially if the medical instrument system is anchored in place. Providing a low-resolution image allows the user to verify that the medical instrument system has not moved. Being able to have a low-resolution imaging system, without the much larger high-resolution system, frees up more space within the medical instrument system for other tools. In one embodiment of the invention, the low-resolution imaging system could be a permanent feature of the medical instrument system as a circumferential series of fiber-optic cables or fibers, thereby freeing up virtually all of the space used to navigate to the target tissue.

Figure 6:
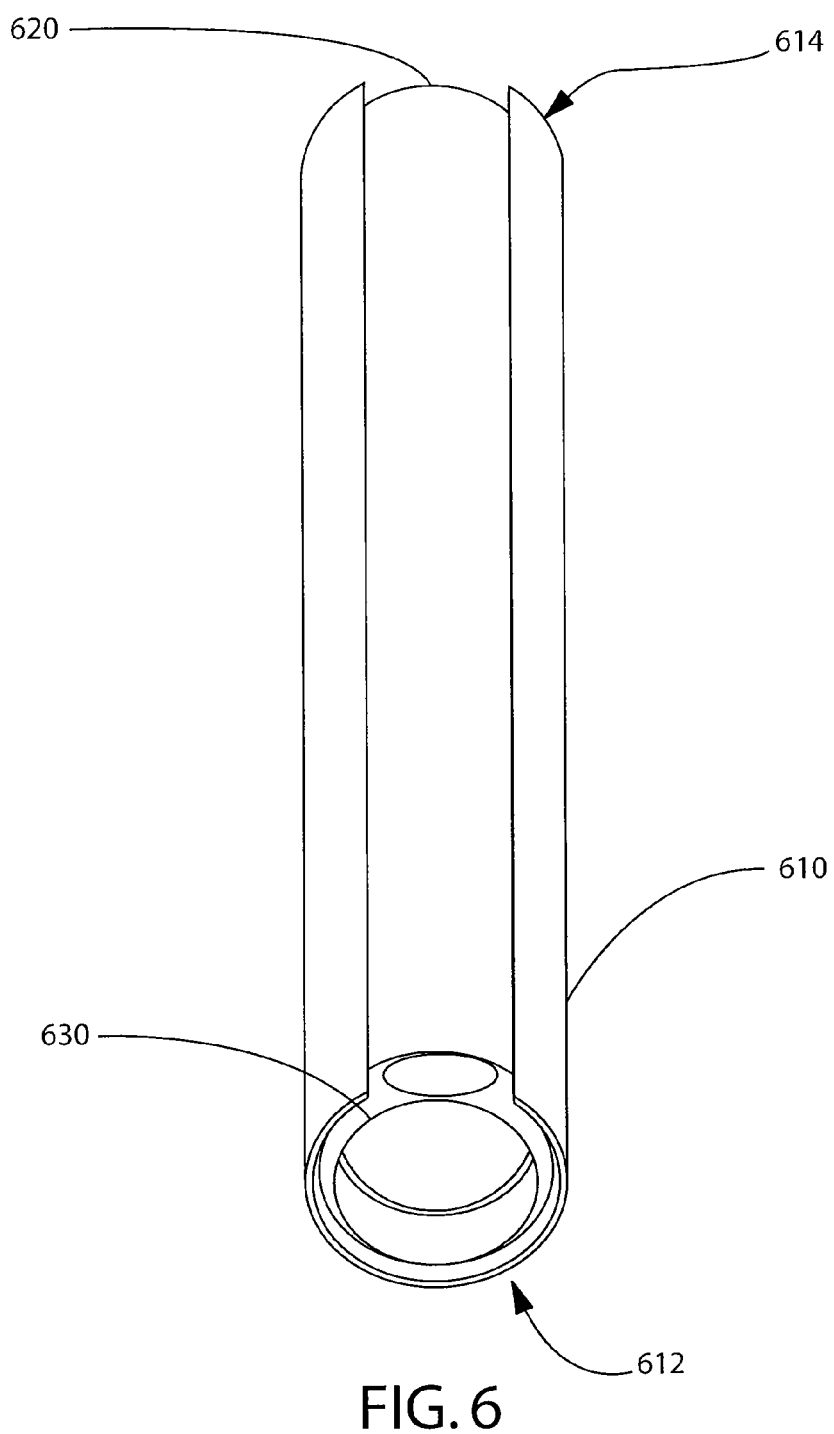
FIG. 6 is a cut-away perspective view of another embodiment of a system for manipulating target tissue of a patient according to an aspect of the present invention, showing a segment of the system together with an anchoring balloon.

As shown in FIG. 6, an interchangeable component 620 is inserted into the working channel 610. Once the interchangeable component 620 has reached the distal end of the working chamber, a suction balloon 630 is inflated behind the proximal end 612 of the interchangeable component 620. When the balloon 630 is inflated it will secure the interchangeable component 620 within the working channel 610, which will resist or prevent axial movement of the interchangeable component 620. Interchangeable component 620 may be placed flush against distal end 614 of the working channel 610 and thereby secured in place to allow for secured uninterrupted target tissue imaging or manipulation.

Although not pictured, the working channel 610 and interchangeable component 620 is optionally provided with an indicator system that will alert the user when the distal end of the interchangeable component 620 has reached the distal end of the working channel 610. This indicator system prevents the distal end of the interchangeable component 620 from exiting the distal end of the working channel 610 and possibly dislodging the entire medical instrument system from its fixed spot on the target tissue. This indicator system may consist of an indicator light, a system of mirrors, a ridge to prevent further movement on the distal end of the working channel, or any other indicator system known in the art.

As discussed above, in some embodiments of the medical instrument system, the scope body will define at least one fixation chamber. Upon insertion of the medical instrument system and the identification of the target tissue, the medical instrument system will be fixed at a location proximal to the target tissue to facilitate insertion and removal of the interchangeable components in the working channels. By fixing distal end of the medical instrument system to the target tissue or at a location fixed in space with respect to the target tissue, the user will prevent the possible movement of the distal end during the exchange of interchangeable components. This in turn will prevent the user from having to re-identify the target tissue. In yet another embodiment of the present invention the proximal end of the medical instrument system may be fixed in three-dimensional space by placing the scope into a scope holder (not shown). Fixing the proximal end of the medical instrument system facilitates the exchange of instruments through he working channel without affecting the medical instrument system position within the viscus. The medical instrument system holder may be a flexible arm that may or may not be secured to the operating room table or another similar device. In another embodiment of the invention, the medical instrument system may utilize any known technique in the art including, but not limited, to magnets, electromagnetic sensors, and/or triangulation.

As described with reference to FIG. 2 above, one means for securing the distal end of the medical instrument system to the target tissue is by applying a vacuum source to the proximal end of the fixation chamber or chambers. By supplying a vacuum to the proximal end of the fixation chamber(s) the medical instrument system will create a vacuum seal between the distal end of the scope and the target tissue. This vacuum may be applied by a vacuum system placed at or coupled to the proximal end of the medical instrument system, or an external vacuum source is optionally connected to the fixation chambers.

Figure 7:
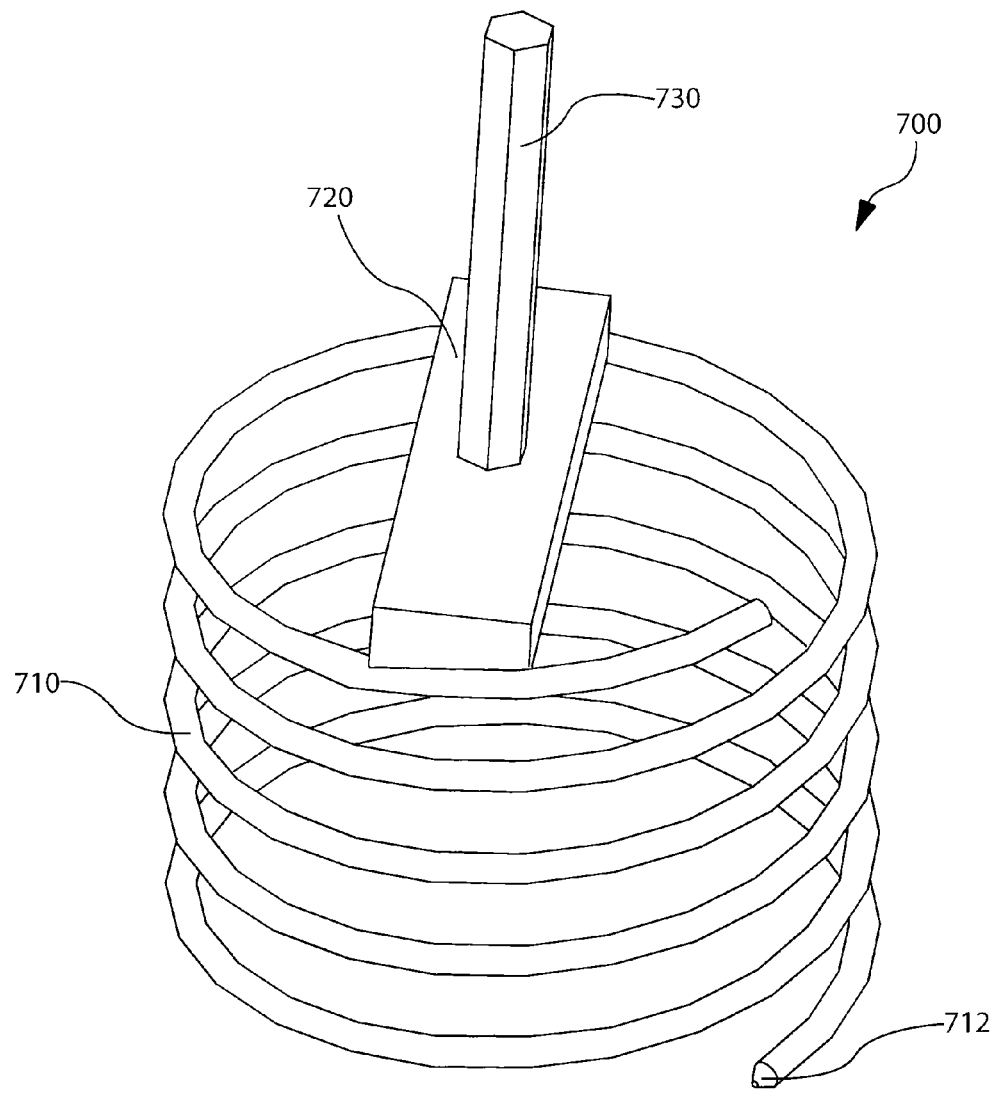
FIG. 7 is a perspective view of an attachment device that may be used in conjunction with embodiments of the present invention.

In an alternative embodiment, shown in FIG. 7, a screw-type fixation device 700 may be deployed through the distal end of the fixation chamber. Screw-type fixation device 700 consists of a coil 710, a mounting bracket 720, and a hexagonal drive-shaft 730. Screw-type fixation device 700 is screwed into the target tissue to fix the medical instrument system to the target tissue. The user will turn hexagonal drive-shaft 730 in a clockwise direction, allowing coil 710 to embed in a patient's tissue starting at coil-point 712. Similarly, to remove screw-type fixation device 700 from tissue that it has been implanted into, the user turns hexagonal drive-shaft 730 in a counter-clockwise manner until coil 710 has emerged from the target tissue.

It will be understood to one skilled in the art, that hexagonal drive-shaft 730 may extend through the fixation chamber to allow the user access at the proximal end of the medical instrument system to turn the coil 710 in either direction. Conversely, a component may be inserted into the fixation chamber and attached to hexagonal drive-shaft 730 to allow coil 710 to be rotated in either direction by the user. Additionally, it will be understood to one skilled in the art that drive-shaft 730 is not limited to merely a hexagonal shape, but rather may be in the form of any shape.

Once the medical instrument system is fixed to the target tissue, such as by fixing the distal end of the system in x-y-z coordinates at or proximal the target tissue, any optics or imaging devices may be removed from the working channel. At this point a medical instrument designed to manipulate the target tissue is inserted into the working channel. In a preferred embodiment of the invention, this medical instrument will be an anchor and sheath coring biopsy device.

Figure 9:
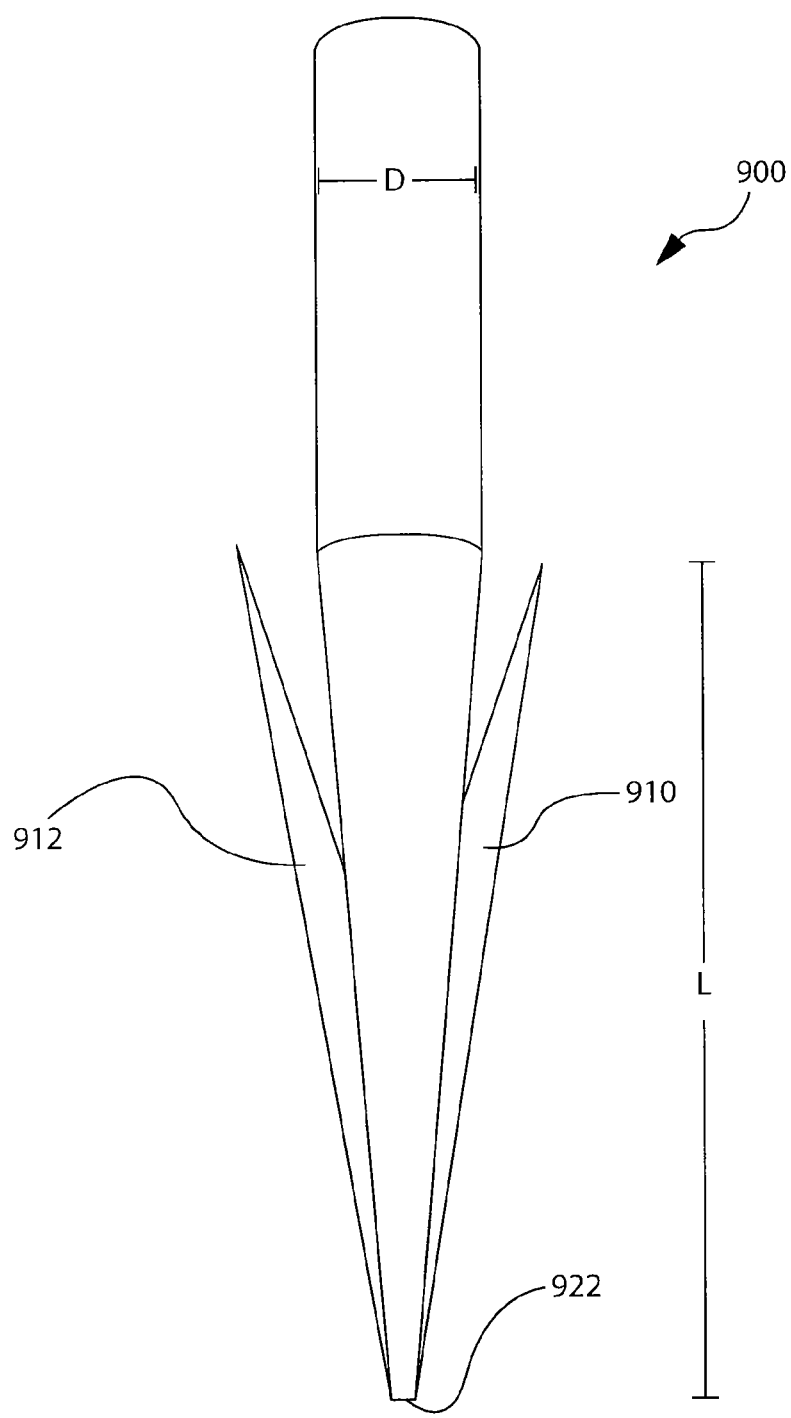
FIG. 9 is a side-view of yet another embodiment of a system for manipulating target tissue of a patient according to an aspect of the present invention, showing an attachment device that may be used in conjunction with embodiments of the present invention.

An embodiment of a procedure for performing a core biopsy is illustrated in FIGS. 8A through 8E. In FIG. 8A, a guide-wire 812 with an anchor 810 is inserted through the working channel and delivered to the surface of the target tissue 820. An expanded view of the anchor component 900 is shown in FIG. 9. After the anchor is delivered to the surface of the target tissue 820, the anchor 810 is then deployed into the target tissue 820 wall as shown in FIG. 8B. This procedure may optionally be done under the guidance of the ultrasound imaging system to regulate the depth that the anchor is deployed to in the target tissue wall. After the anchor 810 is deployed into the target tissue 820 wall, a biopsy sheath 814 is deployed over the guide-wire 812 as illustrated in FIG. 8C. FIG. 8D shows the biopsy sheath 814 as it is united with the anchor 810. Once the sheath 814 is united with the anchor 810, a core of tissue is obtained. The anchor 810, sheath 814 and tissue along with the guide-wire 812 are all removed as a unit as shown in FIG. 8E. This method obviates the need for electrocautery and thus eliminates the cautery artifact that so often limits modern transurethral tumor staging. Indeed, such delivery of core biopsy methodology through a flexible scope into a hollow viscus is novel.

FIG. 9 shows an anchor component 900 with two barbs 910 and 912. Barbs 910 and 912 have a length L. The shaft 920 of anchor component 900 tapers from a diameter D of the shaft to a point 922. The tapered section of the anchor component 900 also has a length L. In one embodiment, anchor component 900 will be attached to a guide-wire and inserted into a patient's tissue. The anchor component 900 will be inserted at least a depth of L so that barbs 910 and 912 will prevent anchor component 900 from inadvertently removing itself from the patient's tissue. In another embodiment of the invention, anchor component 900 may be attached to a component with the fixation chamber. In such an embodiment, anchor component 900 will be used to fix the medical instrument system to the target tissue area.

It is understood that the present invention is in no way limited to just the use of a core biopsy. In another embodiment of this invention, a cold-cut biopsy may be performed. In additional embodiments of the invention, non-biopsy related procedures may be performed.

Figure 10:
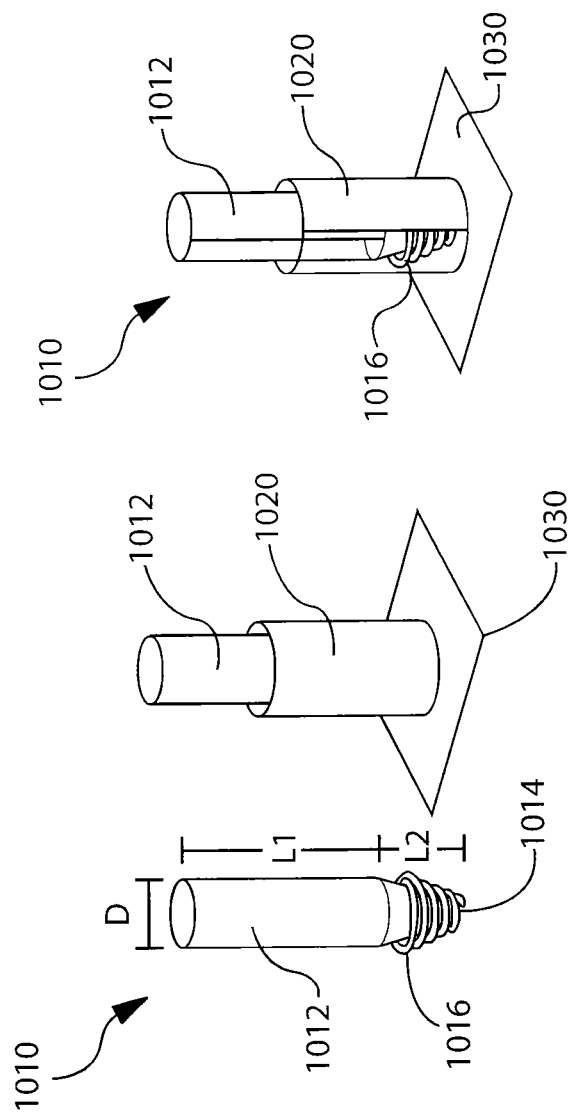
FIG. 10 is a perspective view of still another embodiment of a system for manipulating target tissue of a patient according to an aspect of the present invention, showing an attachment and/or tissue manipulation device that may be used in conjunction with embodiments of the present invention.
Figure 11:
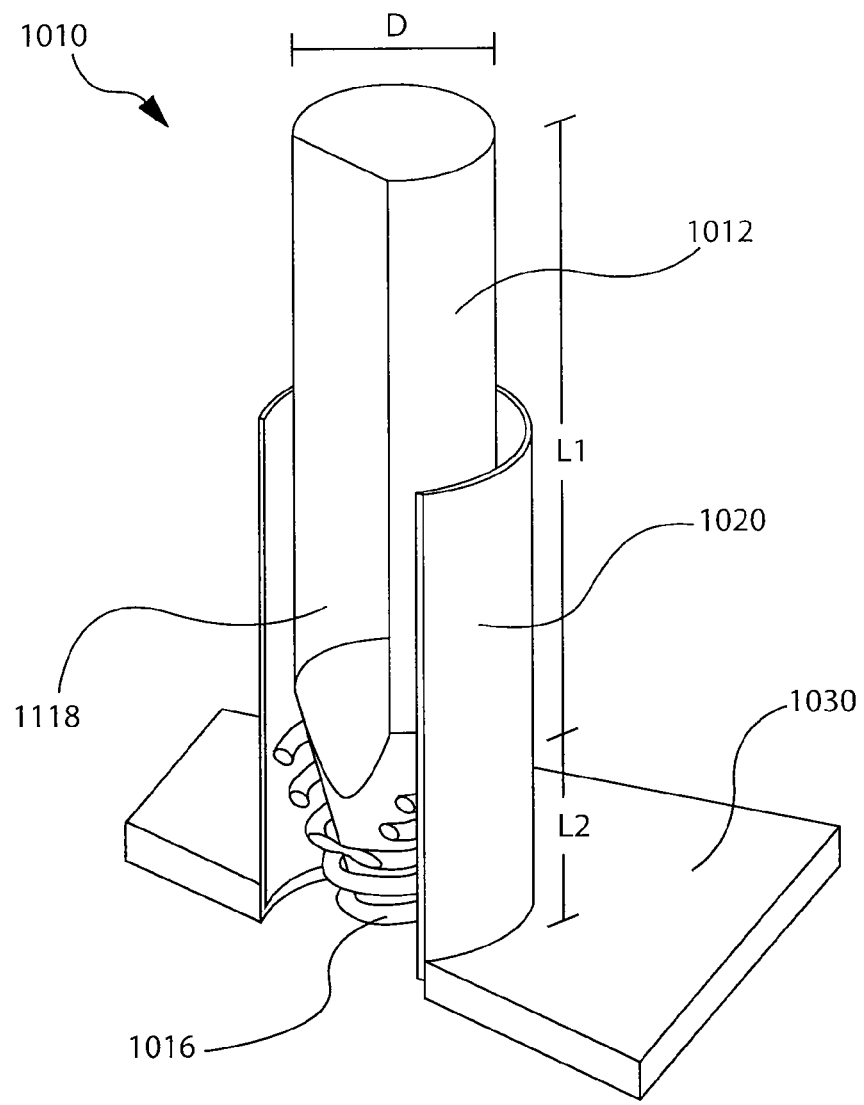
FIG. 11 is an enlarged cut-away view of the system shown in FIG. 10.

FIGS. 10 and 11 show an alternative embodiment of a biopsy procedure that may be performed with the present invention. As depicted in FIG. 10, a coring screw 1010 is inserted in a cannula 1012 that is in contact with the target tissue 1020. Coring screw 1010 consists of a shaft 1012. Shaft 1012 has a diameter D and a length L1. Shaft 1012 tapers to a point 1014 for a distance of L2. The tapered portion of shaft 1012 is surrounded by a coil 1016 that allows coring screw 1010 to be rotated into a patient's target tissue.

In some embodiments of the invention, the coring screw 1010 is placed in a cannula 1020 and rotated in a clockwise direction until it enters the target tissue 1030. In some embodiments of the invention, the coring screw 1010 may be used to as a fixation element to fix the distal end of the medical instrument system into the target tissue. In other embodiments of the present invention, the coring screw 1010 may be used to retrieve a sample of the target tissue into the hollow center 1118 of the coring screw as shown in FIG. 11. To remove the coring screw 1010 from the target tissue, the shaft 1012 of coring screw 1010 is rotated in a counter-clockwise direction until the coil 1016 exits the target tissue 1030. When the coring screw 1010 is used as a coring biopsy device, the coring screw 1010 will be removed from the target tissue 1030 along with the sample target tissue that has been captured by the coring screw 1010.

Figure 12:
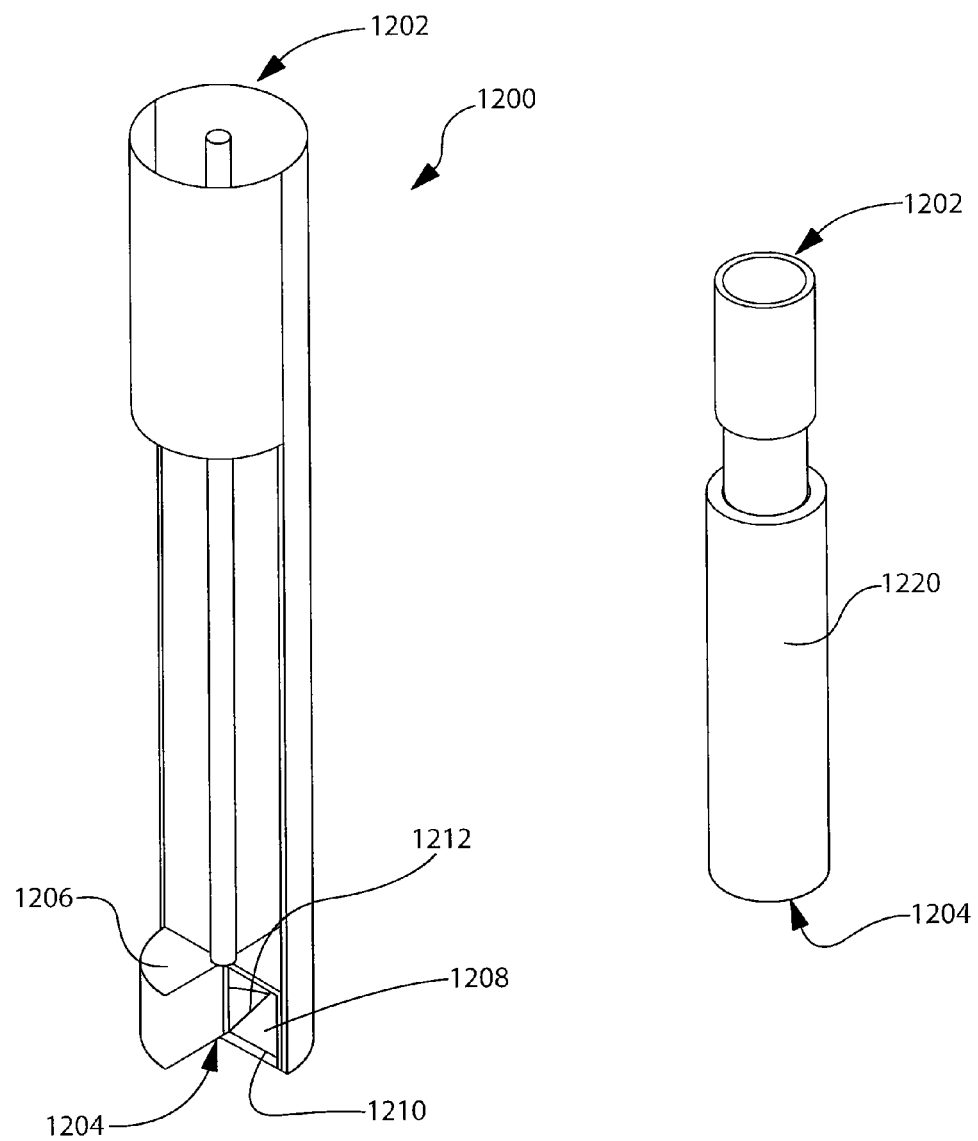
FIG. 12 is a cut-away view of another embodiment of a system for manipulating target tissue of a patient according to an aspect of the present invention, showing a tissue manipulation device that may be used in conjunction with embodiments of the present invention.

FIG. 12 shows yet another embodiment of the present invention, which facilitates the use of a Forstner-type biopsy device 1200. The Forstner biopsy device 1200 is inserted into the working chamber of the medical instrument system. Forstner biopsy device 1200 has a proximal end 1202 and a distal end 1204. The proximal end includes a depth adjustment stop. A bevel edge chamber 1206 is located at distal end 1204. The bevel edge chamber 1206 is opened at the distal end and a screw edge bevel 1208 is located within the bevel edge chamber 1206. Screw edge bevel 1208 contains a cutting edge 1210. In some embodiments of the present invention, the Forstner biopsy device may be secured within the working channel by the use of a suction balloon or some other method of fixation.

In some embodiments of the present invention, the Forstner biopsy device 1200 may be inserted into a cannula 1220 which is then inserted into the working channel of the medical instrument system. In some embodiments of the device, the cannula 1220 may be secured to the target tissue either through the use of suction or another fixation method. The distal end 1204 of the Forstner biopsy device 1200 will be placed against the target tissue area. The user may then rotate the proximal end 1202 of the Forstner biopsy device 1200 in a clockwise direction which will translate to a clockwise rotation in the distal end 1204 of the biopsy device 1200. As the screw edge bevel 1208 is rotated in a clockwise direction, the cutting edge 1210 of the screw edge bevel 1208 cuts a top sample of the target tissue and captures the target tissue in a sample collection space located within the bevel edge chamber 1206. The bevel may be rotated in the clockwise direction until the proximal end depth adjustment stop is reached at which point the cutting edge 1210 becomes a circular scalpel which cuts out a cored section of the target tissue. The bevel edge chamber 1206 is provided with a ridge 1212 which will allow the sample target tissue to be secured within the bevel edge chamber 1206. The Forstner biopsy device 1200 may then be removed from the working channel with the target tissue safely stored inside.

Upon the completion of all procedures relating to the target tissue, the medical instrument system is disengaged from the target tissue by either removing the vacuum suction or other fixation from the proximal end of the fixation chamber or by unfastening or unscrewing a fastener or screw-type fixation device. In addition to fixing the distal end of the medical instrument system, in some embodiments of the present invention, the proximal end of the medical instrument system may be fixed in place to prevent any movement of the medical instrument system.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A medical instrument system for manipulating target tissue of a patient during a medical procedure, the system comprising:
   a) an instrument system body;
   b) a fixation chamber defined by the instrument system body;
   c) an anchor extending in a distal direction from a distal end of the instrument system body, the anchor adapted to releasably secure the distal end of the instrument system body to resist movement with respect to the target tissue by penetrating into the target tissue, such that the distal end of the instrument system body remains at a fixed position near the target tissue, the anchor comprising a tapered portion having a tip and a base and a plurality of barbs directly coupled to the tapered portion and extending from the tip of the tapered portion toward the base of the tapered portion, an entire length of the tapered portion being the same as an entire length of the barbs; and
   d) a sheath movable within the instrument system body, the sheath configured to surround the anchor.

2. The medical instrument system of claim 1 further comprising a girdle surrounding the circumference of the distal end of the instrument system body.

3. The medical instrument system of claim 1 further comprising a low quality optics system located on the instrument system body.

4. The medical instrument system of claim 1 wherein the instrument system body is configured to be flexible.

5. The medical instrument system of claim 4 wherein the instrument system body further comprises deflection wires, said deflection wires configured to aid in flexing the instrument system body.

6. The medical instrument system of claim 1 further comprising a guide wire channel having a set cross-sectional shape defined by the instrument system body.

* * * * *